United States Patent
Hu et al.

(10) Patent No.: US 10,577,364 B2
(45) Date of Patent: Mar. 3, 2020

(54) CRYSTALLINE FORM OF FUSED PYRIDINE DERIVATIVE'S MALEATE AND USES THEREOF

(71) Applicant: BETTA PHARMACEUTICALS CO., LTD, Hangzhou, Zhejiang (CN)

(72) Inventors: Shaojing Hu, Beijing (CN); Wei Long, Beijing (CN); Liufeng Zhou, Beijing (CN); Zhiguo Xu, Beijing (CN); Fei Wang, Beijing (CN)

(73) Assignee: BETTA PHARMACEUTICALS CO., LTD, Hangzhou, Zhejiang (CN)

( * ) Notice: Subject to any disclaimer, the term of this patent is extended or adjusted under 35 U.S.C. 154(b) by 0 days.

(21) Appl. No.: 15/740,719

(22) PCT Filed: Jul. 20, 2016

(86) PCT No.: PCT/CN2016/090613
§ 371 (c)(1),
(2) Date: Dec. 28, 2017

(87) PCT Pub. No.: WO2017/012539
PCT Pub. Date: Jan. 26, 2017

(65) Prior Publication Data
US 2018/0186788 A1 Jul. 5, 2018

(30) Foreign Application Priority Data
Jul. 20, 2015 (WO) ................ PCT/CN2015/084414

(51) Int. Cl.
| | |
|---|---|
| *C07D 471/04* | (2006.01) |
| *A61K 45/06* | (2006.01) |
| *A61K 9/48* | (2006.01) |
| *A61K 31/437* | (2006.01) |
| *A61K 9/20* | (2006.01) |
| *B01D 9/00* | (2006.01) |

(52) U.S. Cl.
CPC .............. *C07D 471/04* (2013.01); *A61K 9/20* (2013.01); *A61K 9/48* (2013.01); *A61K 9/4858* (2013.01); *A61K 31/437* (2013.01); *A61K 45/06* (2013.01); *B01D 9/0054* (2013.01)

(58) Field of Classification Search
CPC .......... C07D 471/04; A61K 9/20; A61K 9/48; A61K 45/06; A61K 9/4858; A61K 31/437; A61K 2300/00; B01D 9/0054; A61P 27/02; A61P 9/00; A61P 35/00; C07B 2200/13
See application file for complete search history.

(56) References Cited

FOREIGN PATENT DOCUMENTS

| | | |
|---|---|---|
| WO | WO-2006/014325 A2 | 2/2006 |
| WO | WO-2010/045095 A1 | 2/2006 |
| WO | WO-2006/116713 A1 | 11/2006 |
| WO | WO-2012/006960 A1 | 1/2012 |
| WO | WO-2014/000713 A1 | 1/2014 |

OTHER PUBLICATIONS

Berge et al (Journal of Pharmaceutical Sciences, p. 1 (Year: 1977).*
International Search Report and Written Opinion issued in corresponding application No. PCT/CN2016/090613 dated Oct. 17, 2016.

* cited by examiner

*Primary Examiner* — Matthew P Coughlin
*Assistant Examiner* — Thurman Wheeler
(74) *Attorney, Agent, or Firm* — Foley & Lardner LLP

(57) ABSTRACT

The compound of Formula I, the crystalline form thereof, and methods of preparing and using them are provided.

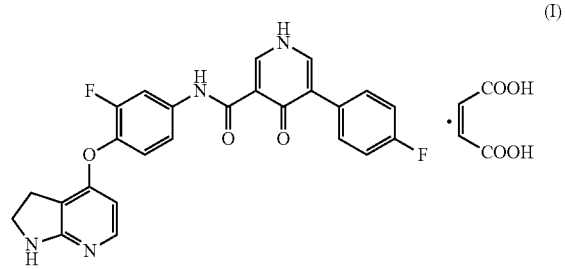

20 Claims, 3 Drawing Sheets

CRYSTALLINE FORM OF FUSED PYRIDINE DERIVATIVE'S MALEATE AND USES THEREOF

CROSS REFERENCE TO RELATED APPLICATIONS

Figure 1:
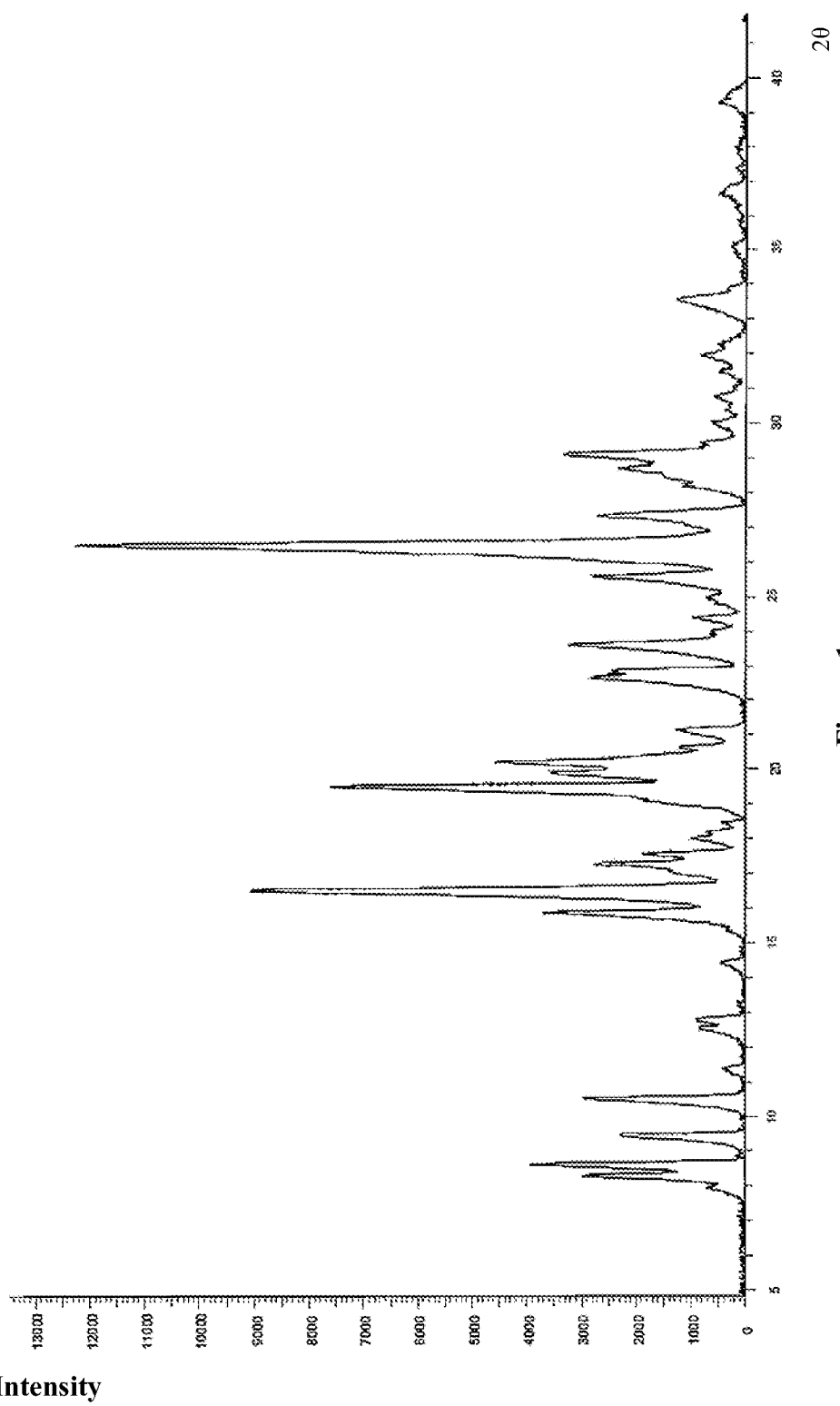

The present application is a national stage entry of International Patent Application No. PCT/CN2016/090613, filed Jul. 20, 2016, which claims priority to International Patent Application No. PCT/CN2015/084414 filed Jul. 20, 2015, each of which is incorporated herein by reference in its entirety.

FIELD OF THE INVENTION

The present invention relates to a new Crystalline Form of fused pyridine derivative's maleate, processes for preparing the new Crystalline Form, pharmaceutical compositions thereof, and use of the new Crystalline Form and pharmaceutical compositions as inhibitors of c-Met, methods for treating a c-Met-mediated disorder.

BACKGROUND OF THE INVENTION

The study of signal transduction pathways in normal and pathological states is of considerable interest because of the potential therapeutic benefit arising from new molecular agents targeting certain of these pathways associated with disease.

Receptor tyrosine kinases (RTKs) are key enzymes in signal transduction pathways that catalyse the autophosphorylation of tyrosine residues within the cytosolic, C-terminal domain of the protein. This generates docking sites for the recruitment of downstream proteins and the subsequent propagation of signals involved in an array of cellular events including growth, proliferation and survival. More generally deregulated kinase signalling is implicated in a diverse range of pathological states including immunological and inflammatory disorders, cardiovascular and neurodegenerative disease. The known receptor tyrosine kinases encompass 20 families and many are oncogenes (Blume-Jensen P et al. 2001. Nature 411 355-365). c-Met is the prototypic member of a subfamily of RTKs which includes the related proteins Ron (macrophage-stimulating protein receptor) and its chicken orthologue, Sea. The endogenous ligand is the growth and motility factor hepatocyte growth factor (HGF, also known as Scatter Factor). c-Met and HGF are expressed in a range of tissue types although their expression is normally restricted to cells of epithelial and mesenchymal origin. In contrast, tumour cells often express constitutively activated c-Met.

There is now a growing body of compelling evidence from both animal studies and cancer patients that HGF-Met signalling plays an important role in the development and progression of malignancy and is associated in particular with invasive phenotypes. c-Met and HGF are highly expressed relative to surrounding tissue in numerous cancers and their expression correlates with poor patient prognosis (Jiang, W et al. 1999 Crit. Rev. Oncol.-hematol., 29, 209-248). Activating point mutations in the kinase domain of c-Met are implicated in the cause of sporadic and hereditary forms of papillary renal carcinoma (Danilkovitch-Miagkova, A et al 2002. 1 J. Clin. Invest. 109, 863-867). c-Met is a marker for both cancer and malignancy and agents that inhibit c-Met-HGF signalling can be expected to ameliorate disease progression in relevant cancers.

Many pharmaceutically active organic compounds can crystallize in more than one type of three-dimensional crystal structure. That is, the compounds may crystallize in different crystalline forms. This phenomenon (identical chemical structure but different crystalline structure) is referred to as polymorphism, and the species having different molecular structures are referred to as polymorphs.

Polymorphs of a particular organic pharmaceutical compound may have different physical properties, such as solubility and hygroscopicity, due to their distinct three-dimensional crystal structures. However, it is generally not possible to predict whether a particular organic compound will form different crystalline forms, let alone predict the structure and properties of the crystalline forms themselves. The discovery of a new crystalline or Polymorph Form of a pharmaceutically useful compound may provide a new opportunity for improving the overall characteristics of a pharmaceutical product. It enlarges the repertoire of materials that a formulation scientist has available for designing. It may be advantageous when this repertoire is enlarged by the discovery of new polymorphs of a useful compound.

WO2014/000713A1 disclosed the structure of N-(4-(2,3-dihydro-1H-pyrrolo[2,3-b]pyridin-4-yloxy)-3-fluorophenyl)-5-(4-fluorophenyl)-4-oxo-1,4-dihydropyridine-3-carboxamid, i.e., Example 1, Product 1, the structure as Formula II:

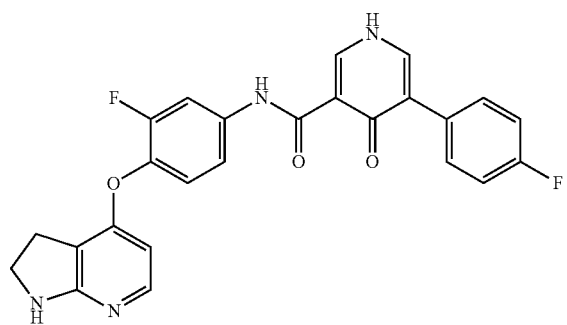

Formula II

SUMMARY OF INVENTION

The present invention relates to fused pyridine derivative's maleate (specifically, N-(4-(2,3-dihydro-1H-pyrrolo[2,3-b]pyridin-4-yloxy)-3-fluorophenyl)-5-(4-fluorophenyl)-4-oxo-1,4-dihydropyridine-3-carboxamide maleate (i.e., the Compound of Formula I)), an approximately pure Crystalline Form thereof.

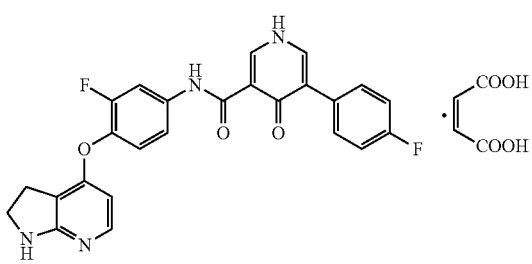

Formula I

The present invention provides a preferable Crystalline Form of Formula I and its X-ray powder diffraction pattern has characteristic peaks at diffraction angles 2θ of approximately 8.6°±0.2°, 16.5°±0.2° and 26.5°±0.2°.

The present invention further provides preferred embodiments of the above Crystalline Form.

Preferably, its X-ray powder diffraction pattern has characteristic peaks at diffraction angles 2θ of approximately 8.6°±0.2°, 15.8°±0.2°, 16.5°±0.2°, 19.5°±0.2°, 20.2°±0.2° and 26.5°±0.2°.

Preferably, its X-ray powder diffraction pattern has characteristic peaks at diffraction angles 2θ of approximately 8.6°±0.2°, 10.5°±0.2°, 15.8°±0.2°, 16.5°±0.2°, 19.5°±0.2°, 20.2°±0.2°, 23.6°±0.2°, 26.5°±0.2° and 29.1°±0.2°.

Preferably, its X-ray powder diffraction pattern is shown as in FIG. 1.

The X-ray diffraction pattern depicted in FIG. 1 is summarized in Table 1.

TABLE 1

| 2θ (2 theta) ± 0.2 (degrees) | d-spacing [Å] | Intensity |
|---|---|---|
| 8.6 | 10.3 | 4225 |
| 10.5 | 8.4 | 3412 |
| 15.8 | 5.6 | 4203 |
| 16.5 | 5.4 | 11270 |
| 19.5 | 4.6 | 8643 |
| 20.2 | 4.4 | 5163 |
| 23.6 | 3.8 | 3745 |
| 26.5 | 3.4 | 14189 |
| 29.1 | 3.1 | 3931 |

Preferably, the Crystalline Form of Formula I has a purity of ≥85%.

Preferably, the Crystalline Form of Formula I has a purity of ≥99%.

Preferably, the Crystalline Form of Formula I has a purity of ≥99.5%.

The present invention also provides a method of preparing the above Crystalline Form of Formula I, comprising the steps of:

Reacting the Compound of Formula II with maleic acid in a reaction media of ethyl acetate (EtOAc) in a glass reactor at room temperature (RT) centrifuged and dried overnight under vacuum at RT to obtain the resulted Crystalline Form;

Formula II

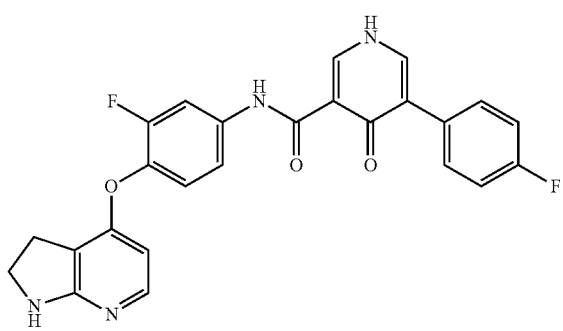

Or

Slurrying excess amount of the Compound of Formula I in a solvent of ethanol (EtOH), acetonitrile (ACN), acetone, EtOAc, isopropyl acetate (IPAc), methyl tert-butyl ether (MTBE), tetrahydrofuran (THF), 2-methyl-tetrahydrofuran (2-MeTHF), 1,4-dioxane, 2-butanone, dichloromethane (DCM), toluene, heptane, isopropanol (IPA), or water ($H_2O$) at RT for 5 days, or in a solvent of ACN, acetone, EtOAc, IPAc, MTBE, 2-MeTHF, 1,4-dioxane, 2-butanone, DCM, toluene, heptane, IPA, or $H_2O$ at 50° C. for 5 days, and recovering the resulted Crystalline Form; or dissolving the Compound of Formula I in a solvent of methanol (MeOH) to get a saturated solution, covering the solution with a film, followed by a spontaneous precipitation at RT, and recovering the resulted Crystalline Form; or dissolving the Compound of Formula I in a mixed solvent of dimethylsulfoxide (DMSO)/EtOH, DMSO/THF, or N-methyl pyrrolidone (NMP)/EtOH with the volume ratio of 1/60, or a mixed solvent of N,N-dimethylformamide (DMF)/EtOH, or DMF/1,4-dioxane with the volume ratio of 1/30, followed by a spontaneous precipitation at RT, and recovering the resulted Crystalline Form; or dissolving the Compound of Formula I in a solvent of DMSO, NMP, or DMF, adding an anti-solvent of $H_2O$, IPAc, ACN, or MTBE, for DMSO, or an anti-solvent of $H_2O$, IPAc, ACN, MTBE, or 2-MeTHF, for NMP and DMF into the former corresponding solution until precipitation being observed, the suspension being kept stirring at RT overnight, and recovering the resulted Crystalline Form; or grinding the Compound of Formula I sufficiently with a solvent of $H_2O$, or a mixed solvent of $H_2O$/ACN, $H_2O$/EtOH, $H_2O$/THF, or $H_2O$/acetone with the volume ratio of 1/1, and recovering the resulted Crystalline Form; or sealing a small glass vial with the Compound of Formula I into a big glass vial containing a solvent of MeOH, ACN, acetone, IPAc, THF, DCM, heptane, or $H_2O$, placing the vials at RT to allow sufficient time for solvent vapor to interact with the solids, and recovering the resulted Crystalline Form; or Dissolving the Compound of Formula I into MeOH to get a saturated solution, and sealing the small glass vial with the former solution into a big glass vial containing an anti-solvent of EtOH, ACN, or $H_2O$ at RT, and recovering the resulted Crystalline Form.

The Crystalline Form of Formula I of this invention unexpectedly exhibited significantly better bioavailability and chemical stability. Accordingly, the invention further provides a pharmaceutical composition comprising a therapeutically effective amount of the Crystalline Form of the present invention, and a pharmaceutically acceptable excipient, adjuvant or carrier, such as hydroxypropyl methyl cellulose. In the composition, the weight ratio of the Crystalline Form to the excipient can be within the range of, e.g., from about 0.0001 to about 10.

The present invention also provides preferable embodiments of the pharmaceutical composition.

Preferably, the pharmaceutical composition comprises a therapeutically effective amount of the Crystalline Form of the present invention, in combination with at least one of additional active ingredient.

Preferably, the pharmaceutical composition is used in an oral administration.

Preferably, the pharmaceutical composition is used in a tablet or a capsule.

Preferably, the pharmaceutical composition comprises 0.01 wt %-99 wt % of the Crystalline Form of the present invention.

Preferably, the pharmaceutical composition comprises 5 wt %-75 wt % of the Crystalline Form of the present invention.

Preferably, the pharmaceutical composition comprises 10 wt %-50 wt % of the Crystalline Form of the present invention The present invention additionally provided a use of the Crystalline Form of Formula I and/or the pharmaceutical composition for the preparation of a medicament.

In some embodiments, a medicament thus prepared can be used for the treatment or prevention of, or for delaying or preventing onset or progression in, cancer, cancer metastasis, cardiovascular disease, an immunological disorder or an ocular disorder.

In some embodiments, a medicament thus prepared can be used for the treatment of a disease mediated by a protein kinase.

In some embodiments, the protein kinase is c-Met, c-Met (D1246H), c-Met (D1246N), c-Met (D1268T), c-Met (D1248C), c-Met (D1248D), c-Met (D1248H), Axl, KDR, DDR2, or RON.

In some embodiments, the disease, the disorder, or the condition mediated by protein kinase activity is cancer.

In some embodiments, the cancer is a solid tumor, a sarcoma, fibrosarcoma, osteoma, melanoma, retinoblastoma, a rhabdomyosarcoma, glioblastoma, neuroblastoma, teratocarcinoma, hematopoietic malignancy, or malignant ascites.

In some embodiments, the cancer is lung cancer, breast cancer, colorectal cancer, renal cancer, pancreatic cancer, head cancer, neck cancer, hereditary papillary renal cell carcinoma, childhood hepatocellular carcinoma, or gastric cancer.

The present invention also provides a method of treating a patient having a disease, a disorder, or a condition which is mediated by protein kinase activity, said method comprising administering to the patient a therapeutically effective amount of the Crystalline Form of Formula I and/or the pharmaceutical composition as described herein.

In some embodiments, the method described herein, the said protein kinase is c-Met, c-Met (D1246H), c-Met (D1246N), c-Met (D1268T), c-Met (D1248C), c-Met (D1248D), c-Met (D1248H), Axl, KDR, DDR2, or RON.

In some embodiments, the method described herein, the disease, the disorder or the condition mediated by protein kinase activity is cancer.

In some embodiments, the method described herein, the said cancer is a solid tumor, a sarcoma, fibrosarcoma, osteoma, melanoma, retinoblastoma, a rhabdomyosarcoma, glioblastoma, neuroblastoma, teratocarcinoma, hematopoietic malignancy, or malignant ascites.

Additionally provided is a method of treating cancer selected from the group consisting of lung cancer, breast cancer, colorectal cancer, renal cancer, pancreatic cancer, head cancer, neck cancer, hereditary papillary renal cell carcinoma, childhood hepatocellular carcinoma, and gastric cancer in a mammal comprising administering to a mammal in need of such treatment an effective amount of the Crystalline Form or the pharmaceutical composition described herein.

In some embodiments, the present invention is directed to a method of treating a patient suffering from c-Met tyrosine kinase-mediated disorders, comprising the step of administering to said patient a therapeutically effective amount of the Crystalline Form of Formula I or the pharmaceutical composition.

The above-described methods can be applied in combination with any chemical therapy, biological therapy or radiation therapy.

The Crystalline Form of the present invention is approximately pure.

The term "approximately pure" as herein used refers to at least 85 wt %, preferably at least 99 wt %, more preferably at least 99.5 wt % of the Compound of Formula I exists in the Crystalline Form of the present invention.

The main peaks described in the Crystalline Form above are reproducible and are within the error limit (the specified value±0.2).

In the present invention, "its X-ray powder diffraction pattern is shown as in FIG. 1" refers to the X-ray powder diffraction pattern that show major peaks as in FIG. 1, wherein major peaks refer to those with the relative intensity greater than 10%, preferably greater than 30%, relative to the highest peak (with its relative intensity designated to be 100%) in FIG. 1.

Crystallization in the present invention is related to dynamics and equilibrium among different Crystalline Forms under certain conditions. Therefore, those skilled in the art will realize that the resulting Crystalline Form depends on the kinetics and thermodynamics of the crystallization process. Under certain conditions (solvent system, temperature, pressure, and the concentration of the compound of the present invention), a Crystalline Form may be more stable than another one (or, actually be more stable than any other Crystalline Forms). However, the Crystalline Forms that are less stable thermodynamically may be favorable in kinetics. The Crystalline Form may also be affected by factors other than kinetics, such as time, impurity distribution, agitation, presence or absence of polymorph seed. For purposes of this invention, various hydrate and solvate forms are included in the scope of "Crystalline Form".

The term "therapeutically effective amount" as herein used, refers to the amount of a compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combination objects for the effective treatment of a disease, a disorder or a condition.

The pharmaceutical composition comprising the compound of the present invention can be administrated via oral, inhalation, rectal, parenteral or topical administration to a subject who needs treatment. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition of the present invention can be produced by the conventional methods in the pharmaceutical field. For example, the active ingredient can be mixed with one or more excipients, then to make the desired formulation.

The "pharmaceutically acceptable carrier" refers to conventional pharmaceutical carriers suitable for the desired pharmaceutical formulation, for example: a diluent, a vehicle such as water, various organic solvents, etc, a filler such as starch, sucrose, etc; a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye. Preferably, the excipient is suitable for desired formulation and administration type.

The term "disease" or "disorder" or "condition" refers to any disease, discomfort, illness, symptoms or indications.

DESCRIPTIONS OF THE FIGURES

FIG. 1: shows the X-ray powder diffraction pattern of the Crystalline Form of Formula I.

Figure 2:
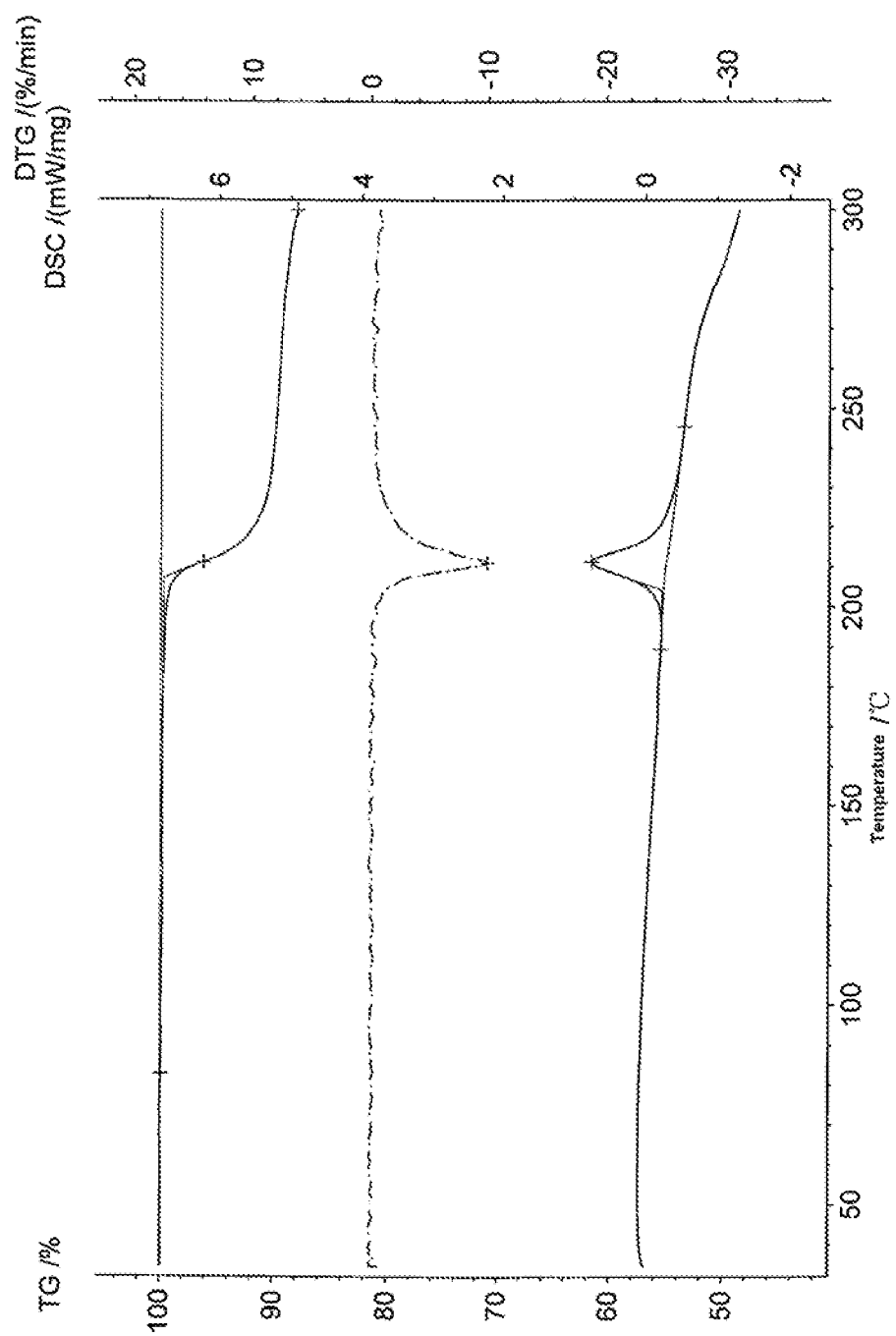

FIG. 2: shows the thermogravimetry-differential scanning calorimetry spectrum of the Crystalline Form of Formula I.

Figure 3:
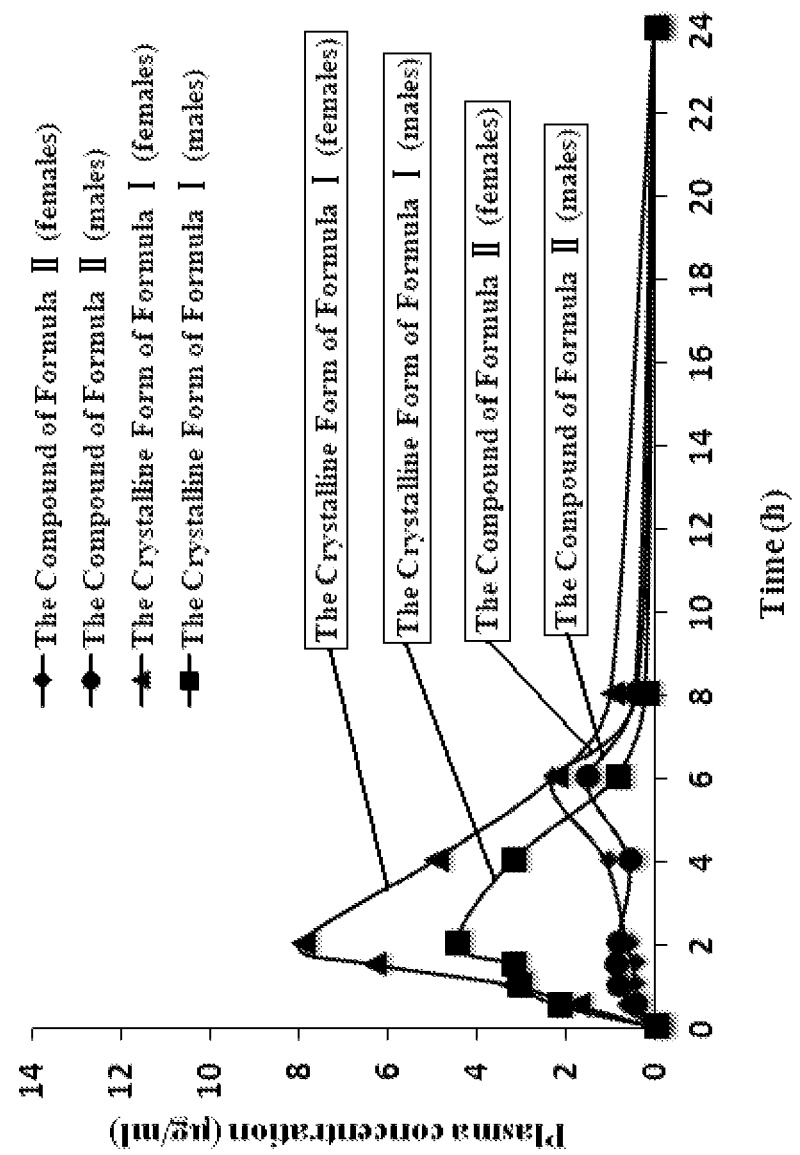

FIG. 3: shows the plasma concentration-time curves of the Compound of Formula II and the Crystalline Form of Formula I.

The X-ray powder diffraction (XRPD) pattern shown as in FIG. 1 was generated on a D8-Advance X-ray Diffraction System. The diffraction peak positions were calibrated by single crystal silicon which has a 2-theta (2θ) value of 28.443 degree. A Cu target X-ray tube K-Alpha radiation was used as the source.

The thermogravimetry-differential scanning calorimetry spectrum shown as in FIG. 2 was generated on a STA449F3 thermal analyzer with the heating rate of 10° C./min and the protective gas of nitrogen.

EXAMPLES

The present invention is further exemplified, but not limited, by the following examples that illustrate the invention. In the examples of the present invention, the techniques or methods, unless expressly stated otherwise, are conventional techniques or methods in the art. The following abbreviations have been used in the examples:

ACN: acetonitrile;
DCM: dichloromethane;
DMF: N,N-Dimethylformamide;
DMSO: dimethyl sulfoxide;
EtOAc: ethyl acetate;
EtOH: ethanol;
HCl: hydrochloric acid
$H_2O$: water;
$IC_{50}$: 50% inhibitory concentration
IPA: isopropanol;
IPAc: isopropyl acetate;
MeOH: methanol;
2-MeTHF: 2-methyl-tetrahydrofuran;
MTBE: methyl tert-butyl ether;
NMP: N-methyl pyrrolidone;
NaCl: sodium chloride
NaOH: sodium hydroxide
THF: tetrahydrofuran;
h or hrs: hour or hours;
m or ms; month or months
rt or RT: room temperature;
RH: relative humidity.

Example 1: Preparation of the Crystalline Form of Formula I 80 mg maleic acid solid was added to 5 mL EtOAc in a glass reactor, stirred till dissolved completely, and then 300 mg the Compound of Formula II was added to the reactor, slurring for 24 hrs at RT, centrifuged and dried overnight under vacuum at RT to obtain the desired Crystalline Form.

Example 2: Preparation of the Crystalline Form of Formula I

A slurry suspension of about 10 mg of the Compound of Formula I was stirred in 0.5 mL solvent of EtOH, ACN, acetone, EtOAc, IPAc, MTBE, THF, 2-MeTHF, 1,4-dioxane, 2-butanone, DCM, toluene, heptane, IPA, or $H_2O$, at RT for 5 days, or in 0.5 mL solvent of ACN, acetone, EtOAc, IPAc, MTBE, 2-MeTHF, 1,4-dioxane, 2-butanone, DCM, toluene, heptane, IPA, or $H_2O$, at 50° C. for 5 days, and recovering the resulted Crystalline Form of Formula I.

Example 3: Preparation of the Crystalline Form of Formula I

About 2 mg of the Compound of Formula I was dissolved in a solvent of MeOH to get a saturated solution, and the solution was covered with a Parafilm™, followed by a spontaneous precipitation at RT, and recovering the resulted Crystalline Form of Formula I.

Example 4: Preparation of the Crystalline Form of Formula I

About 10 mg of the Compound of Formula I was dissolved in 3-6 mL of the mixed solvent of DMSO/EtOH, DMSO/THF, or NMP/EtOH with the volume ratio of 1/60, or the mixed solvent of DMF/EtOH, or DMF/1,4-dioxane with the volume ratio of 1/30, followed by a spontaneous precipitation at RT, and recovering the resulted Crystalline Form of Formula I.

Example 5: Preparation of the Crystalline Form of Formula I

About 10 mg of the Compound of Formula I was dissolved in 0.05-0.1 mL solvent of DMSO, NMP, or DMF, and then an anti-solvent of $H_2O$, IPAc, ACN, or MTBE, for DMSO, or an anti-solvent of $H_2O$, IPAc, ACN, MTBE, or 2-MeTHF, for NMP and DMF was added into the former corresponding solution until precipitation was observed, the suspension being kept stirring at RT overnight, and recovering the resulted Crystalline Form of Formula I.

Example 6: Preparation of the Crystalline Form of Formula I

About 20 mg of the Compound of Formula I was grinded sufficiently with 40 μL solvent of H₂O, or 40 μL the mixed solvent of H₂O/ACN, H₂O/EtOH, H₂O/THF, or H₂O/acetone, with the volume ratio of 1/1, and recovering the resulted Crystalline Form of Formula I.

Example 7: Preparation of the Crystalline Form of Formula I

A small glass vial with about 10 mg of the Compound of Formula I was sealed into a big glass vial containing 3 mL solvent of MeOH, ACN, acetone, IPAc, THF, DCM, heptane, or H₂O and placing the vials at RT to allow sufficient time for solvent vapor to interact with the solids, and recovering the resulted Crystalline Form of Formula I.

Example 8: Preparation of the Crystalline Form of Formula I

About 8 mg of the Compound of Formula I was dissolved into 2 mL MeOH to get a saturated solution, and then the small glass vial with the former solution was sealed into a big glass vial containing 3 mL anti-solvent of EtOH, ACN, or H₂O at RT, and recovering the resulted Crystalline Form of Formula I.

Example 9: Thermodynamic Stability of the Crystalline Form of Formula I

About 500 g of the Crystalline Form of Formula I was placed into a bag of aluminum-plastic composite film, and the bag was stored under stress test conditions of 40° C.±2° C./RH75%±5% for 0 m, 1 m, 2 ms, 3 ms, or 6 ms. The resulted Crystalline Form was determined by XRPD to be purely the Crystalline Form of formula I. The Crystalline Form of formula I was therefore demonstrated to be the thermodynamically stable Crystalline Form of Formula I.

Example 10: Long Term Stability of the Crystalline Form of Formula I

About 500 g of the Crystalline Form of Formula I was placed into a bag of aluminum-plastic composite film, and the bag was stored under conditions of 25° C.±2° C./RH60%±10% for 0 m, 3 ms, 6 ms, 9 ms, 12 ms, 18 ms, 24 ms, or 36 ms. The resulted Crystalline Form was determined by XRPD to be purely the Crystalline Form of formula I. The Crystalline Form of formula I was therefore demonstrated to be the long term stable Crystalline Form of Formula I.

Example 11: Kinetic Solubility of the Crystalline Form of Formula I and N-(4-(2,3-dihydro-1H-pyrrolo[2,3-b]pyridin-4-yloxy)-3-fluorophenyl)-5-(4-fluorophenyl)-4-oxo-1,4-dihydropyridine-3-carboxamide (the Compound of Formula II)

Kinetic solubility of the Crystalline Form of Formula I and N-(4-(2,3-dihydro-1H-pyrrolo[2,3-b]pyridin-4-yloxy)-3-fluorophenyl)-5-(4-fluorophenyl)-4-oxo-1,4-dihydropyridine-3-carboxamide (the Compound of Formula II) was studied in H₂O at RT. After stirring approximate 4 mg solid in per 2 mL H₂O at RT for a set amount of time, 0.6 mL suspension was centrifuged with the residual solids analyzed by XRPD and the concentrations in supernatants measured by high performance liquid chromatography (HPLC). Kinetic solubility of the Crystalline Form of Formula I and the Compound of Formula II was shown in Table 2. As can be seen from Table 2, the Crystalline Form of Formula I showed higher solubility than the Compound of Formula II.

TABLE 2

| | 1 h | | | 4 hrs | | | 24 hrs | | |
|---|---|---|---|---|---|---|---|---|---|
| Starting Solid | Conc. (μg/mL) | pH | Form Change | Conc. (μg/mL) | pH | Form Change | Conc. (μg/mL) | pH | Form Change |
| The Compound of Formula II | 0.8$^a$ | 7.2 | No | 1.1 | 7.3 | No | 0.5$^a$ | 7.3 | No |
| The Crystalline Form of Formula I | 59.0 | 4.3 | No | 47.8 | 4.1 | No | 98.3 | 3.8 | No |

$^a$<LOD, LOD = 1 μg/mL

Example 12: Pharmacokinetic Study of the Crystalline Form of Formula I and N-(4-(2,3-dihydro-1H-pyrrolo[2,3-b]pyridin-4-yloxy)-3-fluorophenyl)-5-(4-fluorophenyl)-4-oxo-1,4-dihydropyridine-3-carboxamide (the Compound of Formula II)

Drugs and reagents: N-(4-(2,3-dihydro-1H-pyrrolo[2,3-b]pyridin-4-yloxy)-3-fluorophenyl)-5-(4-fluorophenyl)-4-oxo-1,4-dihydropyridine-3-carboxamide (the Compound of Formula II) used in this study was of product 1 disclosed by the WO2014/000713. The Compound of Formula II and the Crystalline Form of Formula I were ground to fine particles. The material content (purity) was not less than 99.0%. Sodium carboxymethyl cellulose was medical supply graded.

Experimental animals: SD rats were divided to a Compound of Formula II group and a Crystalline Form of Formula I group, with both groups consisting of three males and three females.

Pharmaceutical preparation: each compound was formulated in 0.5% (w/v) aqueous sodium carboxymethyl cellulose and the final concentration of each compound was 10 mg/mL.

Administration and sample collection: each suspension was administered orally to fasted SD rats at a dose equivalent to 50 mg/kg the Compound of Formula II in a dose volume of 5 mL/kg. The blood samples were collected in EDTA-K pre anticoagulant tubes just before dosing (0 h) and at 0.5, 1, 1.5, 2, 4, 6, 8 and 24 hrs after dosing. The plasma from these samples was separated by centrifugation at 3000 rpm for 10 min at 4° C. The plasma samples were collected and stored at −80° C. until analysis.

Samples were analyzed by HPLC. Chemical ingredients were separated on a C18 DIKMA Platisil column (250×4.6 mm, 5 μm). An Isocratic mobile phase system consisting of acetonitrile-water (55:45) with 0.02 mol/L of sodium dihydrogen phosphate (adjusted pH to 6.0 by using sodium hydroxide solution) employed for sample analysis. The sample injection volume was 20 μL and the detection wavelength was 302 nm. PK profile comparison of the Compound of Formula II and the Crystalline Form of Formula I was summarized in Table 3 and FIG. 3. The Crystalline Form of Formula I showed higher absorption than the Compound of Formula II.

TABLE 3

|  |  | $AUC_{(0-24)}$ (mg/L * h) | $AUC_{(0-\infty)}$ (mg/L * h) | $T_{1/2}$ (h) | $T_{max}$ (h) | $C_{max}$ (mg/L) |
|---|---|---|---|---|---|---|
| The Compound of Formula II | females | 9.7 ± 6.3 | 18.2 ± 4.6 | 4.7 ± 3.7 | 6.0 ± 2.0 | 1.9 ± 1.1 |
|  | males | 10.1 ± 2.9 | 17.1 ± 7.0 | 6.4 ± 2.6 | 4.5 ± 2.6 | 2.2 ± 0.6 |
| The Crystalline Form of Formula I | females | 46.4 ± 21.6 | 49.3 ± 22.2 | 3.7 ± 2.8 | 2.0 ± 0.0 | 7.5 ± 0.7 |
|  | males | 15.9 ± 5.1 | 17.0 ± 6.1 | 1.7 ± 0.9 | 2.7 ± 1.2 | 3.9 ± 0.7 | c-Met relevant tumors and xenograft models c-Met over expression is a common feature for many human tumors, including lung, breast, colorectal, gastric, renal, pancreatic, head and neck[1,2]. c-Met activating mutations in the kinase domain are implicated as the cause for several tumors, such as hereditary papillary renal cell carcinoma, childhood hepatocellular carcinoma, and gastric cancer[3-7]. c-Met inhibitors from Pfizer demonstrated antitumor efficacy in many human xenograft tumors, including U87MG, GTL16, H441, Caki-1, and PC3[8].

1. Christinsen, J G., Burrows, J., and Salgia, R. Cancer Letters 225: 1-26, 2005.
2. Birchmeier, C, Birchmeier, W., Gherardi, E., and Vande Woude, G F. Nat Rev Mol Cell Biol 4: 915-925, 2003.
3. Di Renzo, M F., Olivero, M., Martone, T. Et al. Oncogene 19: 1547-1555, 2000.
4. Lee, J H., Han, S U, Cho, H. et al. Oncogene 19: 4947-4953, 2000.
5. Ma, P C, Kijima, T., Maulik, G. et al. Cancer Res 63: 6272-6281, 2003.
6. Park, W S., Dong, S M., Kim, S Y. et al. Cancer Res 59: 307-310, 1999.
7. Schmidt, L., Duh, F M., Chen, F., et al. Nat Genet 16: 68-73, 1997.
8. Zou, H Y., Li, Qiuhua., Lee, J H., et al. Cancer Res 67: 4408-4417, 2007.

The Crystalline Form of the present invention is preferably formulated as pharmaceutical compositions administered by a variety of routes. Most preferably, such compositions are for oral administration. Such pharmaceutical compositions and processes for preparing the same are well known in the art. See, e.g., REMINGTON: THE SCIENCE AND PRACTICE OF PHARMACY (A. Gennaro, et al, eds., 19th ed., Mack Publishing Co., 1995). The Crystalline Form of Formula I is generally effective over a wide dosage range.

For example, dosages per day normally fall within the range of about 1 mg to about 200 mg total daily dose, preferably 1 mg to 150 mg total daily dose, more preferably 1 mg to 50 mg total daily dose. In some instances dosage levels below the lower limit of the aforesaid range may be more than adequate, while in other cases still larger doses may be employed. The above dosage range is not intended to limit the scope of the invention in any way. It will be understood that the amount of the compound actually administered will be determined by a physician, in the light of the relevant circumstances, including the condition to be treated, the chosen route of administration, the age, weight, and response of the individual patient, and the severity of the patient's symptoms.

Example 13. Formulation of a Hard Gel Capsule

As a specific embodiment of an oral composition, about 100 mg of the Crystalline Form of Example 1-8 is formulated with sufficient finely divided lactose to provide a total amount of about 580 mg to about 590 mg to fill a size 0 hard gel capsule.

Although the present invention has been described in considerable detail with reference to certain preferred versions thereof, other versions are possible. Therefore, the spirit and scope of the invention should not be limited to the description of the preferred versions described herein. Various modifications of the invention, in addition to those described herein, will be apparent to those skilled in the art from the foregoing description. Such modifications are also intended to fall within the scope of the appended claims.

What is claimed is:
1. A Crystalline Form of the Compound of Formula I,

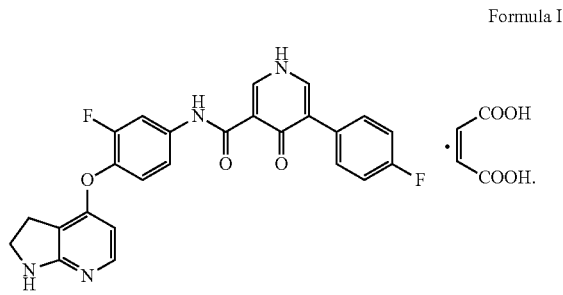

Formula I wherein its X-ray powder diffraction pattern has characteristic peaks at diffraction angles 2θ of 8.6°±0.2°, 16.5°±0.2° and 26.5°±0.2°.

2. The Crystalline Form of claim 1, wherein its X-ray powder diffraction pattern further comprises characteristic peaks at diffraction angles 2θ of 15.8°±0.2°, 19.5°±0.2°, and 20.2°±0.2°.

3. The Crystalline Form of claim 1, wherein its X-ray powder diffraction pattern further comprises characteristic peaks at diffraction angles 2θ of 10.5°±0.2°, 15.8°±0.2°, 19.5°±0.2°, 20.2°±0.2°, 23.6°±0.2°, and 29.1°±0.2°.

4. The Crystalline Form of claim 1, wherein its X-ray powder diffraction pattern is shown as in FIG. 1.

5. The Crystalline Form of claim 1, wherein the Crystalline Form has a purity of ≥85 wt %.

6. The Crystalline Form of claim 1, wherein the Crystalline Form has a purity of ≥99 wt %.

7. The Crystalline Form of claim 1, wherein the Crystalline Form has a purity of ≥99.5 wt %.

8. A method of preparing the Crystalline Form of claim 1, comprising:

a). reacting the Compound of Formula II with maleic acid in a reaction media of ethyl acetate in a glass reactor at room temperature, centrifuged and dried overnight under vacuum at room temperature to obtain the Crystalline Form of claim 1;

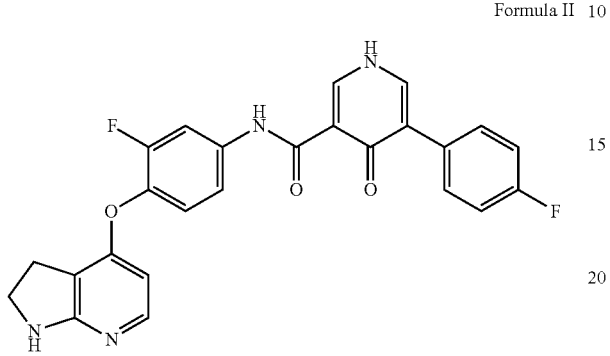

Formula II or b). slurrying excess amount of the Compound of Formula I in the solvent of ethanol, acetonitrile, acetone, ethyl acetate, isopropyl acetate, methyl tert-butyl ether, tetrahydrofuran, 2-methyl-tetrahydrofuran, 1,4-dioxane, 2-butanone, dichloromethane, toluene, heptane, isopropanol, or water at room temperature for 5 days, or in a solvent of acetonitrile, acetone, ethyl acetate, isopropyl acetate, methyl tert-butyl ether, 2-methyl-tetrahydrofuran, 1,4-dioxane, 2-butanone, dichloromethane, toluene, heptane, isopropanol, or water at 50° C. for at least 5 days, and recovering the Crystalline Form of claim 1; or c). dissolving the Compound of Formula I in a solvent of methanol to get a saturated solution, covering the solution with a film, followed by a spontaneous precipitation at room temperature, and recovering the Crystalline Form of claim 1; or d). dissolving the Compound of Formula I in a mixed solvent of dimethylsulfoxide/ethanol, dimethylsulfoxide/tetrahydrofuran, or N-methyl pyrrolidone/ethanol with the volume ratio of 1/60, or a mixed solvent of N,N-dimethylformamide/ethanol, or N,N-dimethylformamide/1,4-dioxane with the volume ratio of 1/30, followed by a spontaneous precipitation at room temperature, and recovering the Crystalline Form of claim 1; or e). dissolving the Compound of Formula I in a solvent of dimethylsulfoxide, pyrrolidone, or N,N-dimethylformamide, adding an anti-solvent of water, isopropyl acetate, acetonitrile, or methyl tert-butyl ether, for dimethylsulfoxide, or an anti-solvent of water, isopropyl acetate, acetonitrile, methyl tert-butyl ether, or 2-methyl-tetrahydrofuran, for pyrrolidone and N,N-dimethylformamide into the former corresponding solution until precipitation being observed, the suspension being kept stirring at room temperature overnight, and recovering the Crystalline Form of claim 1; or f). grinding the Compound of Formula I sufficiently with a solvent of water, or a mixed solvent of water/acetonitrile, water/ethanol, water/tetrahydrofuran, or water/acetone with the volume ratio of 1/1, and recovering the Crystalline Form of claim 1; or g). sealing a small glass vial with the Compound of Formula I into a big glass vial containing a solvent of methanol, acetonitrile, acetone, isopropyl acetate, tetrahydrofuran, dichloromethane, heptane, or water, placing the vials at room temperature to allow sufficient time for solvent vapor to interact with the solids, and recovering the Crystalline Form of claim 1; or h). dissolving the Compound of Formula I into methanol to get a saturated solution, and sealing the small glass vial with the former solution into a big glass vial containing an anti-solvent of ethanol, acetonitrile, or water at room temperature, and recovering the Crystalline Form of claim 1.

9. A pharmaceutical composition comprising a therapeutically effective amount of the Crystalline Form of claim 1, and a pharmaceutically acceptable excipient, adjuvant or carrier.

10. The pharmaceutical composition of claim 9, further comprising a second therapeutically active ingredient.

11. The pharmaceutical composition of claim 9, wherein the pharmaceutical composition is used in an oral administration.

12. The pharmaceutical composition of claim 9, wherein the pharmaceutical composition is used in a tablet or a capsule.

13. The pharmaceutical composition of claim 9, wherein the pharmaceutical composition comprises 0.01 wt %-99 wt % of the Crystalline Form.

14. The pharmaceutical composition of claim 9, wherein the pharmaceutical composition comprises 5 wt %-75 wt % of the Crystalline Form.

15. The pharmaceutical composition of claim 9, wherein the pharmaceutical composition comprises 10 wt %-50 wt % of the Crystalline Form.

16. A method for treating a patient having a disease, a disorder, or a condition mediated by protein kinase activity, comprising administering to the patient in need thereof a therapeutically effective amount of a Crystalline Form of claim 1.

17. The method of claim 16, wherein the protein kinase is c-Met, c-Met (D1246H), c-Met (D1246N), c-Met (D1268T), c-Met (D1248C), c-Met (D1248D), c-Met (D1248H), Axl, KDR, DDR2, or RON.

18. The method of claim 16, wherein the disease, the disorder, or the condition mediated by protein kinase activity is cancer.

19. The method of claim 18, wherein the cancer is a solid tumor, a sarcoma, fibrosarcoma, osteoma, melanoma, retinoblastoma, a rhabdomyosarcoma, glioblastoma, neuroblastoma, teratocarcinoma, hematopoietic malignancy, or malignant ascites.

20. A method of treating cancer in a mammal, comprising administering to the mammal in need thereof a therapeutically effective amount of a Crystalline claim 1, wherein the cancer is selected from the group consisting of lung cancer, breast cancer, colorectal cancer, renal cancer, pancreatic cancer, head cancer, neck cancer, hereditary papillary renal cell carcinoma, childhood hepatocellular carcinoma, or gastric cancer.

* * * * *